US009435675B2

United States Patent
Wise

(10) Patent No.: US 9,435,675 B2
(45) Date of Patent: Sep. 6, 2016

(54) METHOD AND APPARATUS FOR MONITORING, COMMUNICATING, AND ANALYZING THE AMOUNT OF FLUID IN A TANK

(71) Applicant: BreatheWise, LLC, Bridgeville, PA (US)

(72) Inventor: Eric Christopher Wise, Bridgeville, PA (US)

(73) Assignee: BreatheWise, LLC, Bridgeville, PA (US)

( * ) Notice: Subject to any disclaimer, the term of this patent is extended or adjusted under 35 U.S.C. 154(b) by 0 days.

(21) Appl. No.: 14/870,828

(22) Filed: Sep. 30, 2015

(65) Prior Publication Data

US 2016/0097666 A1 Apr. 7, 2016

Related U.S. Application Data

(60) Provisional application No. 62/058,978, filed on Oct. 2, 2014.

(51) Int. Cl.
*G01F 13/00* (2006.01)
*G01F 22/02* (2006.01)
*G01F 1/00* (2006.01)

(52) U.S. Cl.
CPC .............. *G01F 13/006* (2013.01); *G01F 1/00* (2013.01); *G01F 22/02* (2013.01)

(58) Field of Classification Search
CPC ............ G01F 1/74; G01F 1/50; G01F 15/08; G01F 1/00; G01F 22/02; G01F 13/006
See application file for complete search history.

(56) References Cited

U.S. PATENT DOCUMENTS

| 4,718,443 | A |   | 1/1988  | Adney et al. |
|-----------|---|---|---------|--------------|
| 4,987,914 | A | * | 1/1991  | Adney .................... G01F 1/007 137/486 |
| 5,063,734 | A | * | 11/1991 | Morris ...................... F02K 9/56 60/204 |
| 5,297,423 | A |   | 3/1994  | Keating et al. |

(Continued)

FOREIGN PATENT DOCUMENTS

| EP | 2667176 A1 | * | 11/2013 | ........... G01N 29/022 |
|----|-----------|---|---------|------------------------|
| EP | 2848901 A1 | * | 3/2015  | ............. G01G 17/04 |

(Continued)

OTHER PUBLICATIONS

AmeriGas—AccuGas® Remote Tank Monitoring Service web page, http://www.amerigas.com/accugas/default.aspx, 2 pp., 2016.

(Continued)

*Primary Examiner* — John Breene
*Assistant Examiner* — Mohammad Islam
(74) *Attorney, Agent, or Firm* — The Webb Law Firm

(57) ABSTRACT

A device for monitoring the mass of a fluid remaining in a tank as the fluid periodically or continuously leaves the tank includes a housing comprising an inlet adapted to be attached to an outlet of the tank and to receive fluid from the tank. A flow meter measures a plurality of flow rate measurements of the fluid as it leaves the tank. At least one processor is configured to determine a mass of the fluid that has left the tank during at least one measurement period, determine a mass of the fluid remaining in the tank based at least partially on an initial mass of the fluid in the tank and the determined mass of the fluid that has left the tank, and generate, based on the mass of the fluid remaining, an indication.

21 Claims, 4 Drawing Sheets

(56) References Cited

U.S. PATENT DOCUMENTS

| | | | |
|---|---|---|---|
| 5,821,406 A | 10/1998 | Ridgeway et al. | |
| 6,708,573 B1* | 3/2004 | Cohen | F17C 5/007 73/865 |
| 7,574,897 B2 | 8/2009 | Koike et al. | |
| 8,072,340 B2 | 12/2011 | Yukawa et al. | |
| 2002/0138216 A1* | 9/2002 | Taylor | G01F 1/00 702/45 |
| 2004/0129075 A1 | 7/2004 | Sorenson | |
| 2005/0005708 A1* | 1/2005 | Dickes | G01F 17/00 73/861 |
| 2005/0061367 A1* | 3/2005 | Barr | G05D 11/135 137/93 |
| 2006/0130572 A1 | 6/2006 | Northrop | |
| 2007/0204930 A1* | 9/2007 | Phallen | B67D 1/1234 141/83 |
| 2007/0233412 A1* | 10/2007 | Gotoh | G01F 1/6847 702/100 |
| 2008/0147332 A1* | 6/2008 | Arikara | G01F 15/063 702/23 |
| 2008/0150739 A1 | 6/2008 | Gamard | |
| 2009/0019943 A1* | 1/2009 | Ozawa | G01F 1/383 73/861 |
| 2010/0269821 A1* | 10/2010 | Larsson | A61M 16/12 128/202.22 |
| 2011/0220213 A1* | 9/2011 | Cabrera | G01F 1/8413 137/4 |
| 2012/0096923 A1* | 4/2012 | Weinstein | G01F 1/74 73/19.03 |
| 2012/0226451 A1* | 9/2012 | Bacot | G01F 9/008 702/55 |
| 2014/0066880 A1* | 3/2014 | Prince | A61M 5/16881 604/500 |
| 2015/0106039 A1* | 4/2015 | Kwok | G01F 22/02 702/50 |
| 2015/0160057 A1* | 6/2015 | Jo | G01F 1/88 702/47 |

FOREIGN PATENT DOCUMENTS

| | | | |
|---|---|---|---|
| WO | WO 8809484 | * | 12/1998 |
| WO | 2012047862 A1 | | 4/2012 |

OTHER PUBLICATIONS iNetDS literature, https://www.indsci.com/content.aspx?id=2768#Specifications, copyright 2003, 2 pp.

Innovation / Air Liquide—interactions, TAKEO™, a new step for oxygen therapy, http://www.interactions.airliquide.com/eng/april-2014/innovation-115/, Apr. 2014, 1 p.

ISA—Intelligent Sensing Anywhere, http://www.isasensing.com/, 3 pp., 2015.

Linde AG, Genie® Cylinder user manual, www.linde-gas.com/internet.../GENIE_user_manual17_235164.pdf, 3 pp., 2012.

Vendor Managed Gas, VMG Sensor System Descriptions, http://vmg.us.com/documents/VMGSystemDescriptions.pdf, Feb. 19, 2015, 2 pp.

* cited by examiner

METHOD AND APPARATUS FOR MONITORING, COMMUNICATING, AND ANALYZING THE AMOUNT OF FLUID IN A TANK

CROSS REFERENCE TO RELATED APPLICATION

This application claims benefit of priority from U.S. Provisional Patent Application No. 62/058,978, filed Oct. 2, 2014, which is incorporated by reference in its entirety.

BACKGROUND OF THE INVENTION

1. Field of the Invention

The invention relates generally to the monitoring, communication, and analysis of the amount of a fluid in a tank and, more specifically, to a system, method, and apparatus for monitoring, communicating, and analyzing the amount of a fluid in a tank.

2. Description of Related Art

Fluids, in a liquid phase, a gaseous phase, or a combination thereof, are often stored in tanks or other rigid containers. The fluids may be pressurized or at atmospheric pressure. As these fluids leave the tank, it is desirable to know at any given time how much fluid has left the tank, how much fluid remains in the tank, and/or how long until the tank will be empty.

Currently, the flow from many tanks is controlled by a regulator that contains a dial showing the pressure inside of the tank. The change in pressure shown by this dial is often the only indication a user has of how much fluid is left in a tank. The rate at which the dial changes is the only indication a user has of how much time remains until a tank will be empty, and such measurements can prove inaccurate and difficult to read.

In many applications, it is desirable to obtain an accurate estimate of how much fluid is left in a tank, determine how long until that tank will be empty, and communicate and analyze this information. One example is the use of medical oxygen therapy. If a user does not know how much fluid is left in a tank or how long until that tank will be empty, he or she may either run out of oxygen or change the tank before it is necessary. If a medical oxygen supply company does not know exactly which patients need oxygen, how much oxygen they need, and/or when they need the oxygen, they may be required to make inefficient or expensive emergency deliveries.

SUMMARY OF THE INVENTION

Accordingly, it is an object of the invention to provide a method, apparatus, and computer program product for monitoring the mass of a fluid in a tank and providing an indication regarding an amount of the fluid remaining in the tank that overcomes some or all of the deficiencies of the prior art.

According to a preferred and non-limiting embodiment, provided is a method for monitoring the mass of a fluid remaining in a tank as the fluid periodically or continuously leaves the tank, comprising: (a) measuring, with a flow meter in communication with at least one processor, a plurality of flow rate measurements of the fluid as it leaves the tank during at least one measurement period, wherein each flow rate measurement of the plurality of flow rate measurements is determined at a time interval; (b) determining, with the at least one processor, a mass of the fluid that has left the tank during the at least one measurement period based at least partially on: (i) an averaged value of the plurality of flow rate measurements taken during the at least one measurement period, (ii) a density of the fluid at a pressure and/or temperature of the fluid as it passes through the flow meter, and (iii) the time interval between the plurality of flow rate measurements; (c) determining, with the at least one processor, a mass of the fluid remaining in the tank based at least partially on an initial mass of the fluid in the tank and the determined mass of the fluid that has left the tank during the at least one measurement period; and (d) generating, with the at least one processor and based at least partially on the mass of the fluid remaining in the tank, an indication of at least one of the following: a volume of the fluid remaining in the tank, a consumption rate, a consumption rate history, the determined mass of the fluid remaining in the tank, an estimated time remaining before the tank will be empty, or any combination thereof.

In some examples, the method may further include determining, with the at least one processor, the estimated time remaining before the tank will be empty based at least partially on the determined mass of the fluid remaining in the tank, and the average value of the plurality of flow rate measurements taken during the at least one measurement period. Moreover, the pressure and/or temperature of the fluid may be assumed, predetermined, or measured, the density of the fluid at the pressure and/or temperature may assumed or predetermined, and the initial mass of the fluid in the tank may be assumed, predetermined, or measured.

In some embodiments, the method may further include the steps of determining a pressure in the tank with the at least one processor and a pressure sensor in communication with the at least one processor; and determining, with the at least one processor, the initial mass of the fluid in the tank based at least partially on the pressure in the tank and a known, assumed, or determined volume of the tank. The method may also further include the steps of periodically or continuously measuring, with the at least one processor and a pressure sensor in communication with the at least one processor, a pressure inside the tank, resulting in pressure data; determining, with the at least one processor, a rate of change of the pressure in the tank during the at least one measurement period based at least partially on the pressure data; and determining a volume of the tank based at least partially on the rate of change in pressure in the tank during the at least one measurement period and the determined mass of the fluid that has left the tank during the at least one measurement period, wherein the indication further comprises the volume of the tank. In some examples, the rate of change of mass of the fluid is used in the determination. Moreover, the method may also include determining a plurality of volumes of the tank, wherein the initial mass of the fluid in the tank is determined using an average value of the plurality of calculated volumes of the tank. In some examples, the rate of change of the pressure in the tank is determined by conducting a plurality of pressure measurements of the tank at predetermined intervals. The pressure measurements may, in some examples, be averaged. Further, each flow rate measurement may comprise a rolling mean of a plurality of flow rates.

In some embodiments, the method may further include communicating the indication to a remote system or device, where the indication may further comprise information identifying the tank. The indication may also be communicated to a remote system or device, wherein the remote system or device comprises at least one of the following: a robot, a software application configured to plan or predict supply chain events, capital expenses, and/or delivery routes to customers, or any combination thereof. In some examples, the indication may also be communicated to at least one automated valve connected to at least a second tank, wherein the at least one automated valve is configured to open or close based on the indication. In embodiments, the indication may comprise at least one of the following: a visual representation on a display device or graphical user interface, a change in an appearance of a warning light, an audible alarm, an electronically generated voice, a release of a scented gas, an electronic alert, an electronic signal, or any combination thereof.

According to another preferred and non-limiting embodiment, provided is a device for monitoring the mass of a fluid remaining in a tank as the fluid periodically or continuously leaves the tank. The device includes a housing comprising an inlet adapted to be attached to an outlet of the tank and to receive fluid from the tank, and a flow meter configured to measure a plurality of flow rate measurements of the fluid as it leaves the tank during at least one measurement period, wherein each flow rate measurement of the plurality of flow rate measurements is determined at a time interval. The device also includes at least one processor in communication with the flow meter, the at least one processor programmed or configured to: determine a mass of the fluid that has left the tank during the at least one measurement period based at least partially on: an averaged value of the plurality of flow rate measurements taken during the at least one measurement period, a density of the fluid at a pressure and/or temperature of the fluid as it passes through the flow meter, and the time interval between the plurality of flow rate measurements; determine a mass of the fluid remaining in the tank based at least partially on an initial mass of the fluid in the tank and the determined mass of the fluid that has left the tank during the at least one measurement period; and generate, based at least partially on the mass of the fluid remaining in the tank, an indication of at least one of the following: a volume of the fluid remaining in the tank, a consumption rate, a consumption rate history, the determined mass of the fluid remaining in the tank, an estimated time remaining before the tank will be empty, or any combination thereof.

In some embodiments, the at least one processor may be further configured to: determine the estimated time remaining before the tank will be empty based at least partially on the determined mass of the fluid remaining in the tank, and the average value of the plurality of flow rate measurements taken during the at least one measurement period. The at least one processor may also be configured to determine a pressure in the tank with a pressure sensor, and determine the initial mass of the fluid in the tank based at least partially on the pressure in the tank and a known, assumed, or calculated volume of the tank.

In some embodiments, the device may further comprise a pressure sensor in communication with the at least one processor, the pressure sensor configured to periodically or continuously measure a pressure inside the tank, resulting in pressure data. The at least one processor may also be further configured to receive the pressure data, determine a rate of change of the pressure in the tank during the at least one measurement period based at least partially on the pressure data, and determine a volume of the tank based at least partially on the rate of change in pressure in the tank during the at least one measurement period and the determined mass of the fluid that has left the tank during the at least one measurement period, wherein the indication further comprises the volume of the tank. In some examples, the rate of change of mass of the fluid is used in the determination. Further, in some examples the at least one processor may be further configured to determine a plurality of volumes of the tank, wherein the initial mass of the fluid in the tank is determined using an average value of the plurality of determined volumes of the tank. The rate of change of the pressure in the tank may be determined by conducting a plurality of pressure measurements of the tank at predetermined intervals. Further, each flow rate measurement may comprise a rolling mean of a plurality of flow rates.

In some embodiments, the flow meter of the device may be configured to measure flow rate by calculating a rolling mean of a plurality of flow rates. The device may also include a display device disposed in or attached to the housing, the display device configured to display a visual representation based on the indication. Further, the device may also include a communications device disposed in or attached to the housing, the communications device configured to communicate the indication to a remote system or device. The remote system or device may include a robot, a software application configured to plan or predict supply chain events, capital expenses, and/or delivery routes to customers, or any combination thereof. The remote system or device may also include at least one automated valve configured to close and open based on the indication.

According to a further non-limiting embodiment, provided is a non-transitory computer-readable medium for monitoring the mass of a fluid remaining in a tank as the fluid periodically or continuously leaves the tank. The computer-readable medium includes program instructions that, when executed by at least one processor, cause the at least one processor to: measure, with a flow meter in communication with the at least one processor, a plurality of flow rate measurements of the fluid as it leaves the tank during at least one measurement period, wherein each flow rate measurement of the plurality of flow rate measurements is determined at a time interval; determine a mass of the fluid that has left the tank during the at least one measurement period based at least partially on: an averaged value of the plurality of flow rate measurements taken during the at least one measurement period, a density of the fluid at a pressure and/or temperature of the fluid as it passes through the flow meter, and the time interval between the plurality of flow rate measurements; determine a mass of the fluid remaining in the tank based at least partially on a known, measured, or determined initial mass of the fluid in the tank and the determined mass of the fluid that has left the tank during the at least one measurement period; and generate, based at least partially on the mass of the fluid remaining in the tank, an indication of at least one of the following: a volume of the fluid remaining in the tank, a consumption rate, a consumption rate history, the determined mass of the fluid remaining in the tank, an estimated time remaining before the tank will be empty, or any combination thereof.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DETAILED DESCRIPTION

Figure 1:
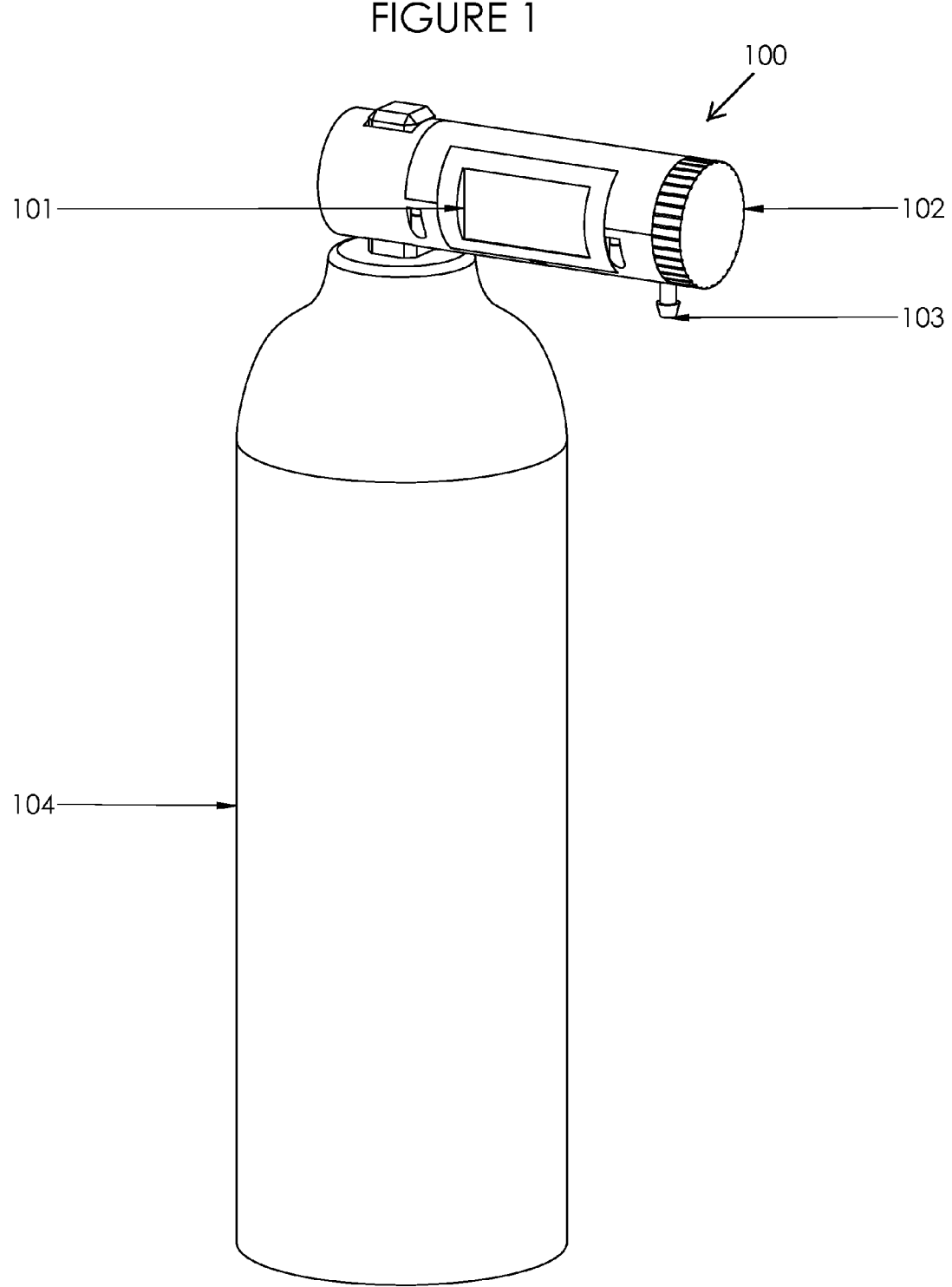
FIG. 1 is a perspective view of a device according to the principles of the present invention.

For purposes of the description hereinafter, the terms "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary configurations of the invention. Hence, specific dimensions and other physical characteristics related to the configurations disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that may be wired and/or wireless in nature. Additionally, two units or components may be in communication with each other even though the data transmitted may be modified, processed, and/or routed between the first and second unit or component. For example, a first unit may be in communication with a second unit even though the first unit passively receives data, and does not actively transmit data to the second unit. As another example, a first unit may be in communication with a second unit if one or more intermediary units processes data from one unit and transmits processed data to the second unit. It will be appreciated that numerous other arrangements are possible.

As used herein, the term indication refers to any conveyance of information which can be perceived by the human senses and/or by a processor or other electronic device in communication with the system whether or not such conveyance of information may also be perceived by a human being. In non-limiting, illustrative examples, an indication may be a signal that can be perceived by sight, hearing, touch, smell, and/or taste. In further non-limiting examples, an indication may be an electronic signal sent to a processor or other electronic device in communication with the system. An indication may also be, for example, data displayed on an interface such as a graphical user interface. In non-limiting embodiments, an electronic device may be configured to perform an action in response to or otherwise based on the receipt of the indication (or lack thereof), or based on information conveyed as part of the indication.

In the examples described herein, non-limiting embodiments of the present invention utilize mathematical formulae based on the ideal gas law. The ideal gas law is largely based on two assumptions. The first is that gas molecules have negligible volume, and the second is that there are no interactions between the gas molecules. Neither of these assumptions is actually true but rather may be used for simplification in non-limiting embodiments of the present invention because the effects of the gas molecules' volume and force interactions are negligible at lower pressures.

For example, at high pressures the assumptions of the ideal gas law are not as useful. The first assumption breaks down because high pressure by definition means a large number of gas molecules in a relatively small space. When this many gas molecules are forced into a small space, their volume becomes relevant as they will begin to resist moving towards each other. The second assumption breaks down because the increased pressure means that the molecules are closer together now and more susceptible to interactions between each other. To account for this, many "real gas" laws have been proposed with perhaps the most famous being van der Waal's equation. These proposed real gas laws tend to still deal with pressure, temperature, moles of gas, and volume, but they also incorporate a number of empirically determined constants that change based on what gas or combination of gases is being evaluated.

It will be appreciated that, particularly in embodiments of the present invention which operate at higher temperatures or pressures, in embodiments wherein the fluid does not generally behave as an ideal gas, or in embodiments wherein the fluid is at least partially in a liquid state, that appropriate adjustments can be made to the calculations and algorithms described in the following non-limiting examples, for example, based on the above-described proposed real gas laws.

FIG. 1 shows an illustration of an assembled device 100 attached to a tank 104 in accordance with a non-limiting embodiment of the present invention. Fluid flows from tank 104 through the device 100 and out of fluid outlet 103. Some aspects of the fluid flow may be controlled with control device 102. During this process, the device measures and determines various aspects of the fluid and tank. The results of these determinations can be shown on display instrumentation 101.

With continued reference to FIG. 1, the tank 104 may be any shape or size such as, but not limited to, a cylindrical tank, a spherical tank, and/or the like. Moreover, the control device 102 may include, as examples, one or more knobs, dials, switches, or the like. The control device 102 in some examples may also be an electronic or software interface, and may be on the device 100 or otherwise in communication with the device 100. Those skilled in the art will appreciate that the fluid outlet 103 may also be any shape or size, and may be located anywhere on the device 100. Various adapters may be connected to the fluid outlet 103 based on how the device 100 is used. The display instrumentation 101 may include, for example, one or more liquid crystal display (LCD) screens, digital displays, light emitting diodes (LEDs), and/or the like. Those skilled in the art will appreciate that the display instrumentation 101 may also be a display screen separate from the device 100 such as, for example, a smartphone or computer monitor in communication with the device.

Figure 2:
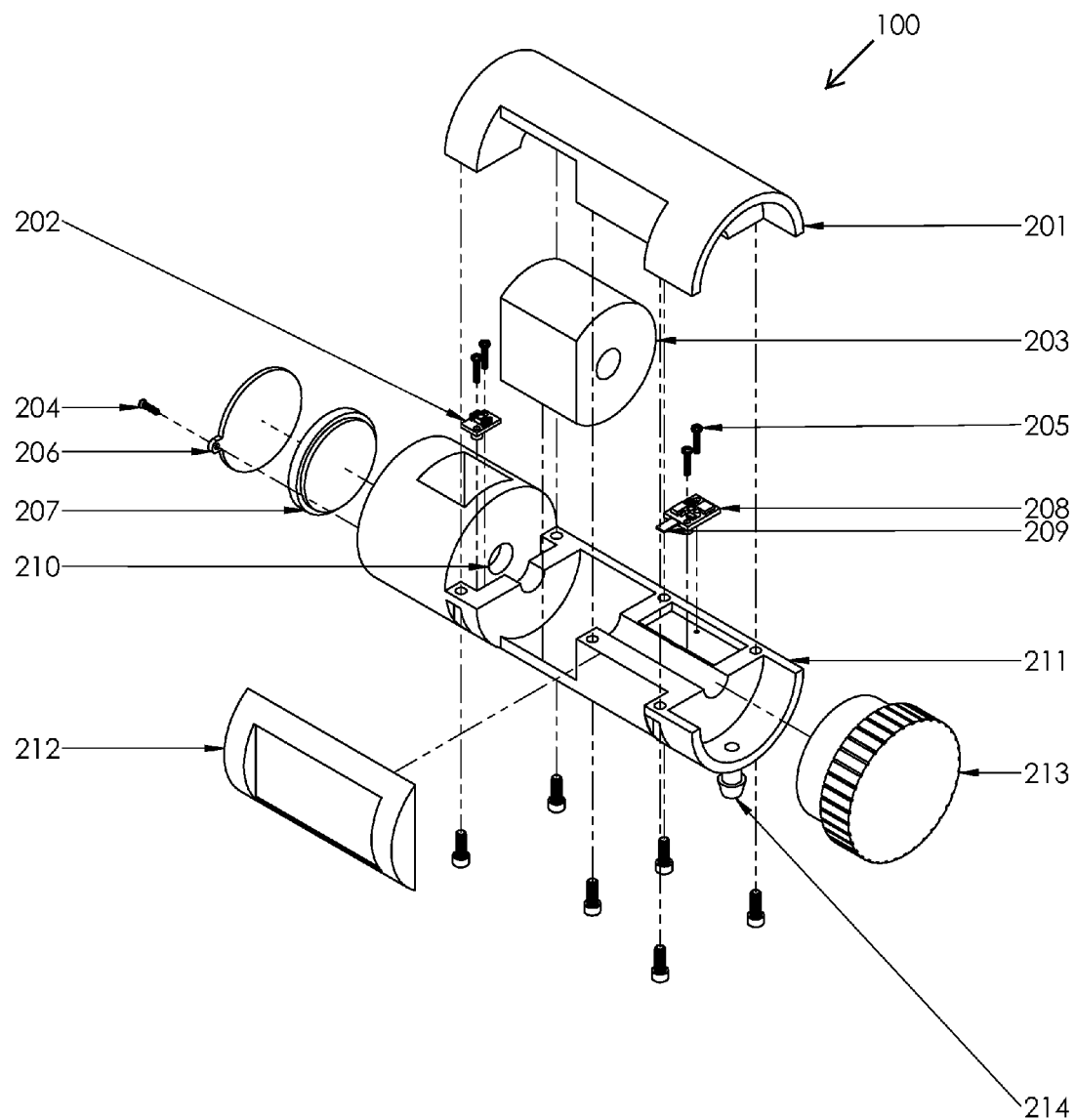
FIG. 2 is an exploded view of the device shown in FIG. 1 according to the principles of the present invention.

FIG. 2 shows an exploded view of the device 100 according to a preferred and non-limiting embodiment. As shown, the fluid enters the device 100 via the fluid intake 210. The fluid then passes into a pressure measuring chamber that contains pressure sensor 202. The device 100 also includes a flow measuring device (e.g., flow meter) 209, control/communication circuitry 208, display instrumentation 212, a control device 213, a pressure regulator 203, and a power source 207. The pressure sensor 202 and/or flow measuring device 209 may be located within the device 100 and in fluid communication with the inlet, or in other examples may be external to the device 100.

With continued reference to FIG. 2, the pressure sensor 202, flow measuring device 209, control/communication circuitry 208, and display instrumentation 212 are powered by the power source 207. This power source 207 could be, but is not limited to, one or more batteries and/or generators utilizing solar energy, wind energy, motion, or thermal energy. Those skilled in the art will appreciate that various other configurations are possible. The power source 207 is disposed in a lower housing 211 of the device 100. The power source 207 is protected by cover 206 which is fastened to lower housing 211 by a fastener 204 such as, but not limited to, screws, nails, rivets, and/or adhesives.

Still referring to FIG. 2, the pressure sensor 202 communicates a signal to the control/communication circuitry 208. This circuitry 208 could include, but is not limited to, a processor such as a microcontroller, microprocessor, or other type of computing device. The processor may have stored thereon, or be in communication with, program instructions that, when executed by the processor, cause the processor to perform data processing tasks. For example, a computer-readable medium may be memory located on or in communication with a processor for storing the program instructions. In non-limiting configurations, the control circuitry 208 could also be divided among a plurality of processors in communication with one another, for example, the control circuitry 208 could be divided into two segments, one in the device and one located external to the device. The circuitry 208 receives signals from the pressure sensor 202 and generates pressure data representing an amount of pressure measured by the device 202.

After passing through the pressure measuring chamber, the fluid flows into pressure regulator 203. The pressure regulator 203 regulates the pressure of the fluid from the pressure of the fluid inside of the tank (not shown) to a predetermined pressure for output through the fluid outlet 214. Next, the fluid flows into a flow measurement channel containing flow measuring device 209. The flow rate of the fluid in this channel can be controlled by the control device 213 or simply be driven by system parameters including, but not limited to, flow demand at the site of fluid use, pressure inside of the tank, or the regulated pressure of the fluid after exiting pressure regulator 203. The flow measuring device 209 sends a signal to the control/communication circuitry 208. The control/communication circuitry 208 may then calculate the mass remaining in the tank and the amount of time until the tank will be empty given that the current flow continues.

In non-limiting embodiments, the circuitry 208 may generate an indication based on the mass remaining in the tank and/or the amount of time until the tank will be empty with the current flow rate. The calculations and algorithms may update very quickly so any large changes in flow affect the time remaining measurement almost instantly. In the non-limiting embodiment shown, the indication generated by the control/communication circuitry 208 is then sent to the display instrumentation 212 which may provide the user with a visual representation of how much of the fluid remains in the tank. The generated indication may also be communicated to an external system or device such as, but not limited to, a computer, database, server, mobile device, additional flow measuring device, or processor, by the control/communication circuitry 208 itself. The indication may also be communicated to a human by any capable device. The indication may be communicated via a network, cellular transmission, radio transmission, Bluetooth® connection, Wi-Fi connection, and/or a tethered (wired) connection, as examples. Those skilled in the art will appreciate that various implementations are possible. Once the communicated indication has been received, it can be analyzed and/or processed by either a human or software program for uses including, but not limited to, route optimization/planning and future asset purchase planning. In the non-limiting embodiment shown, different aspects of the display instrumentation 212 can be changed including, but not limited to, the brightness, color, and/or information on the display.

In the non-limiting embodiment shown in FIG. 2, fluid is introduced into the device 100 via the fluid inlet 210. It will be appreciated that the flow of the fluid through the device 100 could be unidirectional or bidirectional. After exiting the flow measurement channel, the fluid flows out of the device 100 via fluid outlet 214.

In the non-limiting embodiment shown in FIG. 2, the upper housing 201 and the lower housing 211 enclose the device 100 in order to provide protection from damage. The shape of the device 100 shown in the illustration above is cylindrical, but the device 100 could be designed to be any shape. The housings 201, 211, pressure sensor 202, flow measuring device 209, and control/communication circuitry 208 are held together by fasteners 205 such as, but not limited to, screws, nails, rivets, and/or adhesives.

Figure 3:
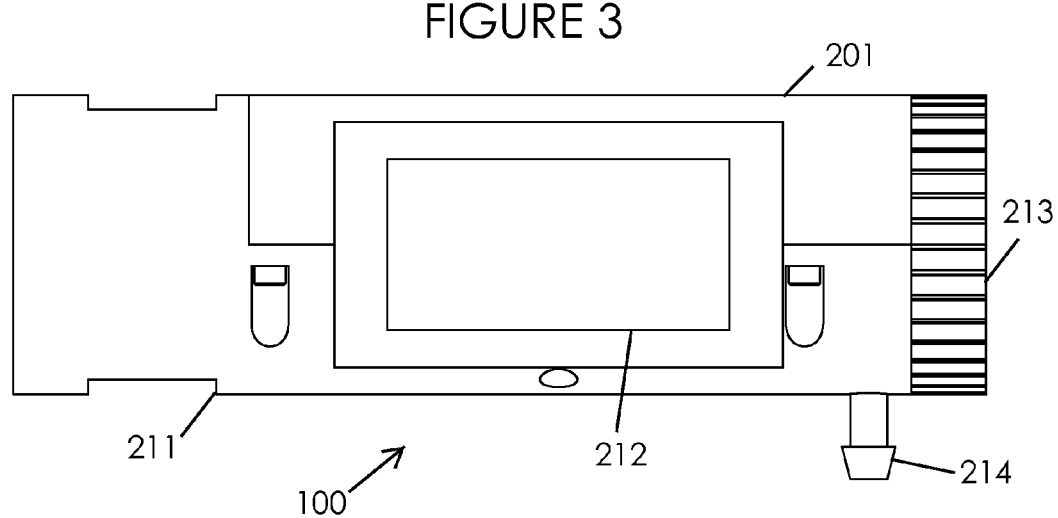
FIG. 3 is a front view of the device shown in FIG. 1 according to the principles of the present invention.

FIG. 3 shows a front view of the device 100 according to a preferred and non-limiting embodiment. As shown, the device includes a control device 213, upper housing 201, lower housing 211, display instrumentation 212, and fluid outlet 214.

Figure 4:
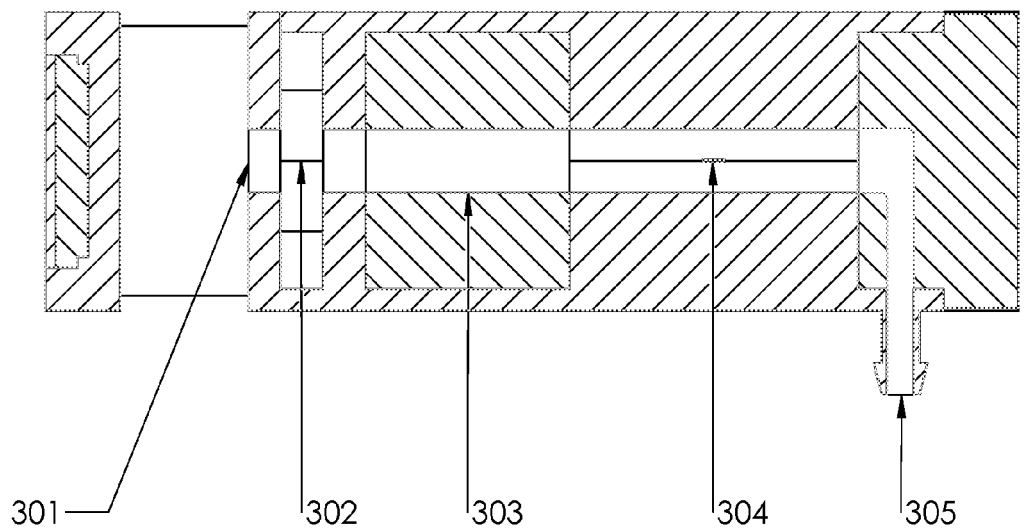
FIG. 4 is a cross-sectional view of the device shown in FIG. 1 according to the principles of the present invention.

FIG. 4 shows a cross-sectional view of the device 100 according to a preferred and non-limiting embodiment. In particular, FIG. 4 illustrates a flow path of the fluid passing through the device 100. The fluid enters fluid inlet 301. The fluid then passes into the pressure measuring chamber 302 that contains pressure sensor 202 (shown in FIG. 2). Next, the fluid passes into the pressure regulator 303. After exiting pressure regulator 303, the fluid enters flow measurement channel 304 that contains flow measuring device 209 (shown in FIG. 2) and control/communication circuitry 208 (shown in FIG. 2). Finally, the fluid exits the device via flow outlet 305.

In non-limiting embodiments, the device 100 may also incorporate a pressure sensor and/or thermometer for measuring a pressure and/or temperature of the fluid inside the tank, a pressure sensor and/or thermometer for measuring a pressure and/or temperature of the fluid as it leaves the tank, or any combination thereof. It will be appreciated that these are optional features, and that in many applications pressure and/or temperature may affect the density of the fluid, may be presumed, or may be estimated in accordance with non-limiting embodiments of the present invention.

In a non-limiting embodiment of the present invention, the amount of the fluid remaining in the tank may be determined using a starting pressure and/or temperature inside the tank as determined by a pressure sensor and using a known, assumed, estimated, or calculated volume of the tank. From this information, the ideal gas law, and/or other fluid dynamics equations known to those skilled in the art, the initial mass in the tank may be determined using a processor in or in communication with the device 100.

Figure 5:
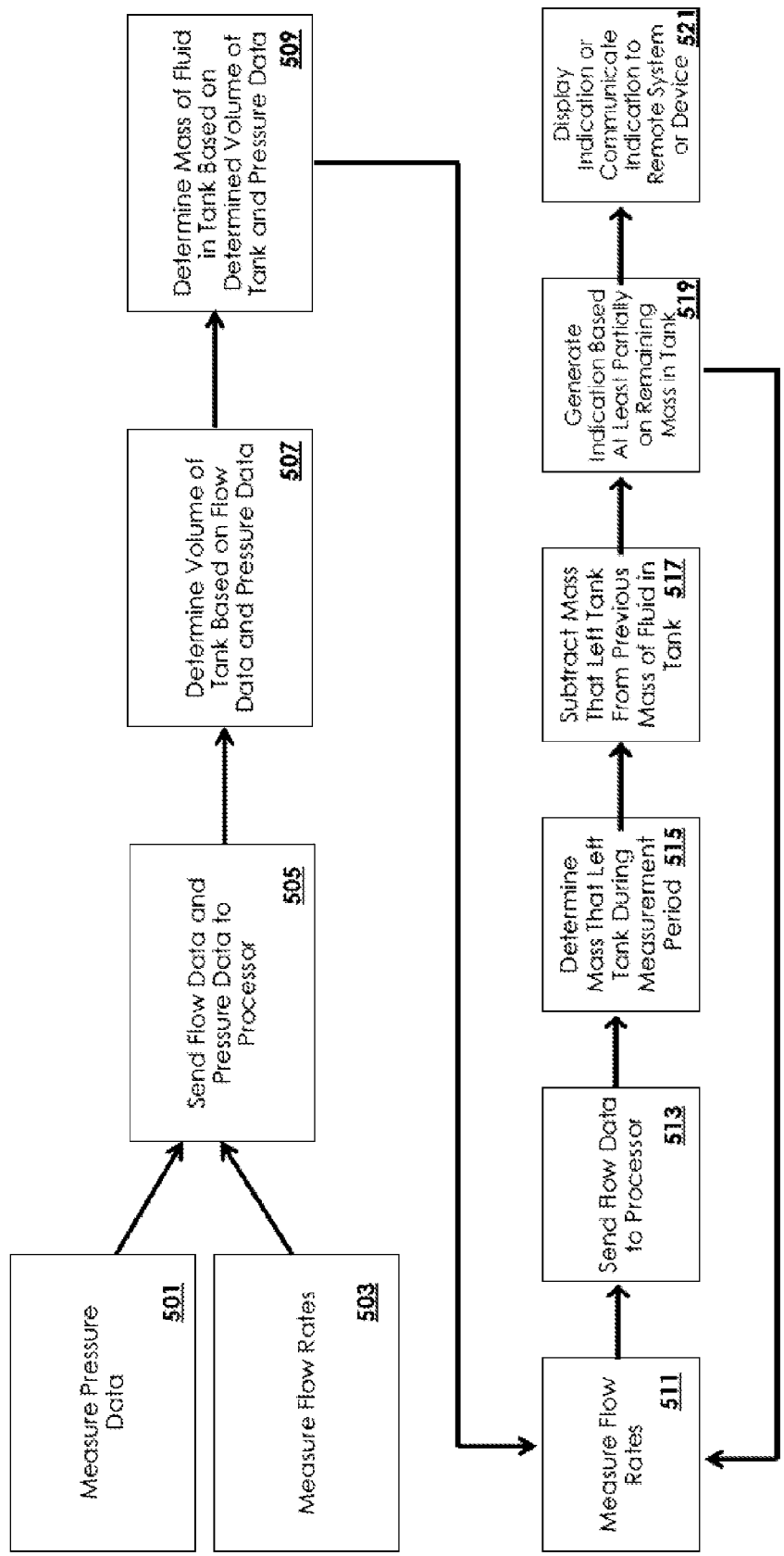
FIG. 5 is a flow diagram for a method according to the principles of the present invention.

Referring to FIG. 5, a flow diagram is shown for a method according to a preferred and non-limiting embodiment. The method starts at steps 501, 503 where pressure data and flow rates are measured with respective pressure and flow measuring devices. At step 505, the flow rate data and pressure data are sent to a processor and, at step 507, a volume of the tank is determined based on that data. At a next step 509, the mass of fluid in the tank is determined based on the determined volume of the tank and the pressure data. The flow rate is measured again, or continually, at step 511, and the flow data is sent to the processor at step 513. At step 515, the processor determines the mass that left the tank during the measurement period. The processor then, at step 517, subtracts the mass that left the tank from the previous mass of fluid in the tank. At step 519, the processor generates an indication based at least partially on the remaining mass in the tank that was determined. The indication may then be displayed or communicated to a remote device or system at step 521.

In the non-limiting embodiment shown in FIG. 2, as the fluid flows out of the tank it passes through the flow measuring device 209, the flow measuring device 209 determines the volumetric flow rate of the fluid leaving the tank at a given time and communicates this value to the control/communication circuitry 208. It will be appreciated that non-limiting embodiments of the present invention may utilize a variety of different types of flow measuring devices which may utilize a variety of physical or chemical properties in order to measure flow rate. In non-limiting examples, the device 100 may utilize flow measuring devices which measure the flow rate based on a mechanical displacement, heat transfer, light interruption, changes in electrical resistance, capacitance or other material property, ultrasonic sensing, or any combination thereof. It is also possible to use a temperature sensor as a flow measuring device, either with or in place of the flow meter to obtain a measurement of the fluid flow rate.

In non-limiting embodiments, the flow rate measurement may be taken a plurality of times in rapid succession. For example, the flow rate measurement may be taken at least two times per second. Generally, providing shorter time intervals between measurements improves the accuracy of the device and, in preferred, non-limiting embodiments, the time interval between measurements is less than ten (10) seconds. It will be appreciated that a variety of time intervals may be used, and that the intervals may exceed ten (10) seconds. These measurements may be averaged to provide a flow rate to be used in the algorithms disclosed herein. Using an average flow rate may serve to reduce noise which may occur in discrete flow measurements.

In a non-limiting, illustrative example, suppose the flow meter in conjunction with a processor takes ten (10) measurements per second and the data points identified in the measurement period are: [4, 4, 3, 4, 5, 4, 4, 5, 4, 3]. In a preferred, non-limiting embodiment, the flow rate used in the algorithms would be the arithmetic mean of the data points identified in the measurement period, in this case, four (4).

In a further preferred and non-limiting embodiment, the flow rate may be normalized over multiple measurement periods, for example, using a rolling average method. In a non-limiting, illustrative example, following the previous example, suppose the next flow rate reading from the sensor is 14. Then, the numbers in the previous array may be shifted to the left with the first number being removed such that the array reads: [4, 3, 4, 5, 4, 4, 5, 4, 3, 14]. In accordance with this example, the next flow rate used in the next cycle of calculations would then be the arithmetic mean of the new array, in this case, five (5). This process may be repeated a plurality of times in rapid succession such that each flow rate used in the algorithms has been normalized to reduce noise. It will be appreciated that a variety of other non-limiting methods to reduce noise and/or normalize the measurements could be used including, but not limited to, medians, modes, standard deviations, integration methods, and the application of filters and/or masks on the data set.

In non-limiting embodiments, the processor may use a normalized flow rate for each cycle and multiply it by the density of the fluid in order to determine a mass flow rate of the fluid (i.e., the amount of mass of the fluid leaving the tank in a given amount of time). The mass flow rate may then be multiplied by the time between sample readings (in the preceding example using a rolling average, this would be 0.1 seconds) in order to determine the mass of the fluid that has left the tank in between sample readings. The mass that left the tank may then be subtracted from the calculated mass in the tank from the previous reading. For example, if there were seven (7) units in the tank before this reading and five (5) units left the tank during the reading, there will be two (2) units in the tank. The time remaining until the tank is empty may then be determined by dividing the remaining mass in the tank by the mass flow rate.

In non-limiting embodiments, the mass remaining in the tank, the size of the tank, and/or the determined time remaining until the tank is empty, may then be utilized to provide the user, a computer, and/or a remote system with an indication of how much fluid is left in the tank, the size of the tank, and/or the determined time remaining until the tank is empty.

In a non-limiting, illustrative example of how the previously described process may operate, suppose a tank is 0.001 cubic meters and the pressure of the fluid inside the tank (in this example, compressed oxygen gas) is measured, for example, by a pressure gauge, at 2000 psi (13,789,514 Pa).

The initial mass in the tank may be calculated by $PV=nRT$, where P is the pressure in the tank, V is the volume of the tank, n is the number of moles of oxygen in the tank, R is the gas constant, and T is the temperature inside of the tank. R is a known constant and T is assumed to be 20° C. (293 Kelvin). The number of moles initially in the tank is therefore:

$$n = \frac{PV}{RT} = \frac{(13,789,514 \text{ Pa})(0.001 \text{ m}^3)}{\left(\frac{8.3144621 \text{ Pa} * \text{m}^3}{\text{K} * \text{mol}}\right)(293 \text{ K})} = 5.66 \text{ moles of oxygen}$$

This result may be multiplied by the molar mass of oxygen to determine the mass of the gas:

$$566 \text{ moles of oxygen} * 0.0319988 \frac{\text{kg}}{\text{mole of oxygen}} = 0.181 \text{ kg of oxygen}$$

In a non-limiting, illustrative example, suppose the flow meter in conjunction with a processor collects a new measurement every 0.1 seconds and averages this value along with the nine (9) previous values. In a non-limiting, illustrative example, the first 10 readings may be (in cubic meters per second): [0.001, 0.001, 0.0011, 0.001, 0.0012, 0.0012, 0.0009, 0.001, 0.001, 0.0011]. The average of these values is 0.00105. This value is then used for this iteration of calculations. When the next sensor reading comes in, the first number in the array is deleted and the new number is added to the end. This new array may be used for the next iteration of calculations.

Accordingly, if the averaged flow rate is 0.00105 cubic meters, the processor may multiply this by the density of oxygen to find the mass flow rate:

$$\frac{0.00105 \text{ m}^3}{\text{s}} * \frac{1.331 \text{ kg}}{\text{m}^3} = 0.00139 \text{ kg/s}$$

This value may then be multiplied by the time interval between measurements:

$$\frac{0.00139 \text{ kg}}{\text{s}} * 0.1 \text{ s} = 0.000139 \text{ kg}$$

This calculation results in the amount of mass that left the tank in the time interval between these measurements.

The processor may then subtract this value from the initial mass amount:

0.181 kg−0.000139 kg=0.180861 kg

The processor may then divide this resulting amount by the mass flow rate to determine the time remaining until the tank is empty:

$$\frac{0.180861 \text{ kg}}{0.00139 \text{ kg/s}} = 130.1 \text{ seconds until empty}$$

In non-limiting embodiments, the processor, or another processor in communication therewith, may be programmed or configured to provide a user, computer, and/or remote system with an indication related to the amount of fluid left in the tank based on the determined mass of the fluid remaining in the tank and/or the determined time remaining before the tank is empty.

In non-limiting examples, the indication may comprise a visual display showing an amount of mass of the fluid left, a percentage of mass of the fluid left, a time remaining before the tank needs to be replaced, or a combination thereof.

In further non-limiting examples, the indication may comprise an audial or visual alarm when the percentage of mass, or time remaining, reaches a predetermined threshold. In non-limiting examples, the alarm may be an audible alarm or a computer generated or pre-recorded voice indication of how much fluid remains in the tank. In non-limiting examples, the alarm could also be a message sent to a mobile device, a visual representation on a graphical user interface, and/or the like.

In further non-limiting examples, the indication may comprise an alarm when the device's power source is running low. In non-limiting examples, the alarm may be an audible alarm or a computer generated or pre-recorded voice indication of how much power is left in the power source (e.g., a percentage of battery charge or a time remaining). In non-limiting examples, the alarm could also be a message sent to a mobile device, a visual representation on a graphical user interface, and/or the like.

In further non-limiting examples, the indication may be sent to one or more other devices and/or systems. Upon receipt of this indication, the one or more other devices and/or systems could use the information contained in the indication as input data for an additional process such as, but not limited to, delivery route optimization/planning and future asset purchase planning.

In further non-limiting examples, the device may also receive an indication sent from one or more other devices and/or systems. These indications could include items such as, but not limited to, software updates to the device, location information, information about the fluid being used with the device, and a device identity number or name. Upon receipt of this indication, the device may then automatically or with manual input update itself or perform a task based on the information in the indication.

Additionally, or alternatively, the indication may cause a device in communication with the device to cause a mechanical change. In a non-limiting example, when the tank is determined to be low or empty, the device may switch to an alternate tank using, for example, an automated valve or robot. In such examples, the indication may trigger an automated valve to open or close.

In accordance with a further non-limiting embodiment of the present invention, the system may be further adapted to determine the volume of the tank and further to determine the mass of the fluid remaining in the tank based at least partially on this determined volume. This produces a distinct advantage in that the device can be applied to multiple tanks of varying geometry or to tanks of unknown geometry without adjusting or entering initial information into the device or adjusting the programming of the device. In this manner, the device may be used for many different tanks and many different purposes.

In a non-limiting embodiment, the pressure inside of a tank that is filled with a gas is approximated using the ideal gas law. This law states that:

$$PV=nRT \quad (1)$$

where P is the pressure inside of the tank, V is the volume of the tank, n is the number of moles of gas in the tank, R is the gas constant, and T is the temperature of the gas/tank. By rearranging the terms in equation 1, it may be found that:

$$P = \frac{nRT}{V} \quad (2)$$

R is a constant term in this equation. V is also a constant term when the tank has a fixed and/or constant volume. In this equation, T is not typically a constant. However, in non-limiting applications such as medical oxygen delivery systems, calibration gas uses, and industrial and specialty gas settings, T may be assumed to be a constant of room temperature because the tanks are primarily used indoors and the variation among temperatures suitable for human habitation or work is generally small enough that it does not substantially affect the determined volume of the tank. However, it is noted that the internal temperatures of the tanks are not necessarily the same as the respective room temperatures.

In non-limiting applications, wherein fluctuations of T are great enough that the determined volume is significantly affected, a thermometer in communication with the device may be incorporated and the measured temperature may be utilized in determining the volume.

It can be seen then that by differentiating both sides of the equation with respect to time, the change in P is directly proportional to the change in n:

$$\frac{d(P)}{dt} = \frac{d\left(\frac{nRT}{V}\right)}{dt} \quad (3)$$

$$\frac{dP}{dt} = \frac{RT}{V}\left(\frac{dn}{dt}\right) \quad (4)$$

Because dP/dt and dn/dt, have been calculated by the processor, and R and T are known constants (or if T is also a known value as determined by a thermometer in communication with the processor), then V can be solved for as follows:

$$V = \frac{\left(\frac{dn}{dt}\right)RT}{\left(\frac{dP}{dt}\right)} \quad (5)$$

In this non-limiting embodiment, the processor may be configured to keep track of a plurality of measurements from the pressure sensor and calculate dP/dt as follows:

$$\frac{dP}{dt} \approx \frac{(P_1 - P_2)}{\Delta t} \quad (6)$$

where $P_1$ is the pressure at one point in time, $P_2$ is the pressure at a later point in time, and $\Delta t$ is the time between $P_1$ and $P_2$.

Generally, providing smaller time intervals between measurements improves the accuracy of the device, and, in preferred non-limiting embodiments, the time interval between pressure measurements is less than 10 seconds, and, in some examples, at least 2 times per second.

A volumetric flow reading from the flow measuring device may then be multiplied by the density of the gas (which may be a presumed constant based on the operating temperature and pressure of the device or which may be determined using a measured temperature and pressure) and the resulting value divided by the molar mass of the gas in order to determine the molar flow rate of the gas. For short periods of time, this is approximately the same as dn/dt.

$$\frac{dn}{dt} \approx \frac{m\rho}{M} \quad (7)$$

where m is the measured volumetric flow rate, p is the density of the gas, and M is the molar mass of the gas.

The preceding equations may be combined to obtain:

$$V \approx \frac{RTm\rho\Delta t}{M(P_1 - P_2)} \quad (8)$$

In non-limiting embodiments, a processor in or in communication with the device may be configured to repeat this calculation several times and average the results in order to determine an estimate of the volume of the tank without having any prior knowledge of the tank size or volume. In non-limiting embodiments, this may be done extremely quickly by a microprocessor such that the volume of the tank may be estimated before the corresponding loss of gas from the tank significantly affects the determined initial mass of the fluid. Once the volume has been determined and used to determine the initial mass of the fluid in the tank by solving equation (1) with the determined volume, assumed or measured pressure, and assumed or measured temperature, the system may proceed to monitor the mass of the fluid remaining in the tank as described above.

In an additional non-limiting embodiment, a pressure of the fluid may be measured as it leaves the tank or very shortly after it has left the tank, either alternatively to, or in addition to, measuring the flow rate of the fluid as it leaves the tank. It is noted that this pressure measurement is different from the measurement of the pressure in the tank itself, and that the pressure of the fluid generally tends to decrease as it flows in a conduit away from the tank.

In this non-limiting embodiment, to determine the mass leaving the tank and determine the remaining mass, a combination of a pressure measuring device (e.g., a pressure sensor or other like device), microcontroller, and computer may be used. As the fluid from the tank flows past the pressure sensor, the sensor may record the fluid pressure and send the data to a processor such as a microcontroller. The processor then may interface with a second processor, for example a personal computer, configured to determine the remaining mass in the tank using software such as Matlab® or other like software.

In this non-limiting example, the mass of the fluid remaining in the tank may be determined as follows:

$$\frac{P_1}{\rho} + \frac{V_1^2}{2} + gz_1 = 2\left(\frac{P_2}{\rho} + \frac{V_2^2}{2} + gz_2 + h_{maj}\right),$$

$$\text{Where } h_{maj} = \frac{fLV^2}{2d_1g}$$

After substitution and simplification, $$\frac{P_1 - P_2}{2\rho} = \frac{fLV^2}{2d_1g}$$

$$V = \sqrt{\frac{d_1 g \Delta P}{fL\rho}}, \text{ where } \Delta P = P_1 - P_2$$

To determine mass transfer in a time interval $\Delta t$, multiply velocity by a time interval $\Delta t$, density, and the cross sectional area of the conduit at that point.

$$VA\rho\Delta t = m$$

$$m = \sqrt{\frac{d_1 g \Delta P}{fL\rho}} \frac{\pi d_2^2}{4}\rho\Delta t = \sqrt{\frac{d_1 g \Delta P \rho}{fL}}\left(\frac{\pi d_2^2 \Delta t}{4}\right)$$

Due to laminar flow, $$f = \frac{64}{Re_d}$$

-continued $$m = \sqrt{\frac{d_1 g \Delta P \rho Re_d}{64L}} \left(\frac{\pi d_2^2 \Delta t}{4}\right)$$

where $Re_d$ is Reynolds number of the fluid.

This equation closely approximates the mass, m, leaving the tank in a time interval of $\Delta t$. By subtracting m from the total mass in the tank, the remaining mass is found. Repetition of this process multiple times per minute allows for a seemingly continuous monitoring of the tank's mass, which may be used to provide an indication or communication of how much time is left before the tank will be empty.

The device described herein has applications in many fields. These applications include, but are not limited to, using the device to display or send information about the state of a compressed gas in a container, using the device to display or send information about the state of a medical oxygen tank, using the device to display or send information about the state of an oxygen tank used by firefighting or emergency response personnel, using the device to display or send information about the state of an oxygen tank used by scuba divers, using the device to display or send information about the state of an industrial and/or specialty gas tank, using the device to display or send information about the state of a propane gas tank such as those used by grills, using the device to send information about how much gas a specific customer such as a medical patient, commercial consumer, or industrial gas consumer currently has on his, her, or its premise, using the device to send information about how much gas a specific customer such as a medical patient, commercial consumer, or industrial gas consumer currently has on his, her, or its premise for delivery route planning and route optimization, using the device to send information about how much gas a specific customer such as a medical patient, commercial consumer, or industrial gas consumer currently has on his, her, or its premise for planning the purchase of capital equipment or targeted customer advertising, using the device to send information about how much gas a specific customer such as a medical patient, commercial consumer, or industrial gas consumer currently has on his, her, or its premise to a software program that analyzes the consumption patterns of large groups of customers, and using the device to send information about how much gas a specific customer such as a medical patient, commercial consumer, or industrial gas consumer currently has on his, her, or its premise to a software program that helps plan supply chain events and/or delivery routes to customers.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for monitoring the mass of a fluid remaining in a tank as the fluid periodically or continuously leaves the tank, comprising:

(a) measuring, with a flow meter in communication with at least one processor, a plurality of flow rate measurements of the fluid as it leaves the tank during at least one measurement period, wherein each flow rate measurement of the plurality of flow rate measurements is determined at a time interval, and wherein the flow meter is disposed in a housing comprising an inlet adapted to be connected to an outlet of the tank such that the flow meter measures the plurality of flow rate measurements after the fluid leaves the tank and flows through a pressure regulator;

(b) determining, with the at least one processor, a mass of the fluid that has left the tank during the at least one measurement period based at least partially on: (i) an averaged value of the plurality of flow rate measurements taken during the at least one measurement period, (ii) a density of the fluid at a pressure and/or temperature of the fluid as it passes through the flow meter, and (iii) the time interval between the plurality of flow rate measurements;

(c) periodically or continuously measuring, with the at least one processor and a pressure sensor in communication with the at least one processor, a pressure inside the tank, resulting in pressure data;

(d) determining, with the at least one processor, a rate of change of the pressure in the tank during the at least one measurement period based at least partially on the pressure data;

(e) determining, with the at least one processor, a volume of the tank based at least partially on the rate of change in pressure in the tank during the at least one measurement period and the determined mass of the fluid that has left the tank during the at least one measurement period;

(f) determining, with the at least one processor, an initial mass of the fluid in the tank based at least partially on an initial pressure in the tank and the volume of the tank;

(g) determining, with the at least one processor, a mass of the fluid remaining in the tank based at least partially on the initial mass of the fluid in the tank and the determined mass of the fluid that has left the tank during the at least one measurement period;

(h) generating, with the at least one processor and based at least partially on the mass of the fluid remaining in the tank, an indication of at least one of the following: a volume of the fluid remaining in the tank, a consumption rate, a consumption rate history, the determined mass of the fluid remaining in the tank, an estimated time remaining before the tank will be empty, or any combination thereof; and (i) communicating the indication to a remote system or device, wherein the remote system or device comprises at least one of the following: a robot, an automated valve configured to open or close based on the indication, a software application configured to plan or predict supply chain events, capital expenses, and/or delivery routes to customers, or any combination thereof.

2. The method of claim 1, further comprising: determining, with the at least one processor, the estimated time remaining before the tank will be empty based at least partially on the determined mass of the fluid remaining in the tank, and the average value of the plurality of flow rate measurements taken during the at least one measurement period.

3. The method of claim 1, wherein the pressure and/or temperature of the fluid is assumed, predetermined, or measured, wherein the density of the fluid at the pressure and/or temperature is assumed or predetermined, and wherein the initial mass of the fluid in the tank is assumed, predetermined, or measured.

4. The method of claim 1, wherein the indication further comprises the volume of the tank.

5. The method of claim 1, further comprising: determining a plurality of volumes of the tank, wherein the initial mass of the fluid in the tank is determined using an average value of the plurality of calculated volumes of the tank.

6. The method of claim 1, wherein the rate of change of the pressure in the tank is determined by conducting a plurality of pressure measurements of the tank at predetermined intervals.

7. The method of claim 1, wherein each flow rate measurement comprises a rolling mean of a plurality of flow rates.

8. The method of claim 1, wherein the indication further comprises information identifying the tank.

9. The method of claim 1, wherein the remote system or device comprises the automated valve connected to at least a second tank.

10. The method of claim 1, wherein the indication comprises at least one of the following: a visual representation on a display device or graphical user interface, a change in an appearance of a warning light, an audible alarm, an electronically generated voice, a release of a scented gas, an electronic alert, an electronic signal, or any combination thereof.

11. A device for monitoring the mass of a fluid remaining in a tank as the fluid periodically or continuously leaves the tank, comprising:
a housing comprising an inlet adapted to be attached to an outlet of the tank and to receive fluid from the tank;
a flow meter disposed in the housing and configured to measure a plurality of flow rate measurements of the fluid after it leaves the tank and flows through a pressure regulator during at least one measurement period, wherein each flow rate measurement of the plurality of flow rate measurements is determined at a time interval;
a pressure sensor in communication with the at least one processor, the pressure sensor configured to periodically or continuously measure a pressure inside the tank, resulting in pressure data; and
at least one processor in communication with the flow meter and the pressure sensor, the at least one processor programmed or configured to:
determine a mass of the fluid that has left the tank during the at least one measurement period based at least partially on: an averaged value of the plurality of flow rate measurements taken during the at least one measurement period, a density of the fluid at a pressure and/or temperature of the fluid as it passes through the flow meter, and the time interval between the plurality of flow rate measurements;
receive the pressure data;
determine a rate of change of the pressure in the tank during the at least one measurement period based at least partially on the pressure data;
determine a volume of the tank based at least partially on the rate of change in pressure in the tank during the at least one measurement period and the determined mass of the fluid that has left the tank during the at least one measurement period;
determine an initial mass of the fluid in the tank based at least partially on an initial pressure in the tank and the volume of the tank;
determine a mass of the fluid remaining in the tank based at least partially on the initial mass of the fluid in the tank and the determined mass of the fluid that has left the tank during the at least one measurement period;
generate, based at least partially on the mass of the fluid remaining in the tank, an indication of at least one of the following: a volume of the fluid remaining in the tank, a consumption rate, a consumption rate history, the determined mass of the fluid remaining in the tank, an estimated time remaining before the tank will be empty, or any combination thereof; and
communicate the indication to a remote system or device, wherein the remote system or device comprises at least one of the following: a robot, an automated valve configured to open or close based on the indication, a software application configured to plan or predict supply chain events, capital expenses, and/or delivery routes to customers, or any combination thereof.

12. The device of claim 11, wherein the at least one processor is further configured to: determine the estimated time remaining before the tank will be empty based at least partially on the determined mass of the fluid remaining in the tank, and the average value of the plurality of flow rate measurements taken during the at least one measurement period.

13. The device of claim 11, wherein the indication further comprises the volume of the tank.

14. The device of claim 11, wherein the at least one processor is further configured to: determine a plurality of volumes of the tank, wherein the initial mass of the fluid in the tank is determined using an average value of the plurality of determined volumes of the tank.

15. The device of claim 11, wherein the rate of change of the pressure in the tank is determined by conducting a plurality of pressure measurements of the tank at predetermined intervals.

16. The device of claim 11, wherein the flow meter is configured to measure flow rate by calculating a rolling mean of a plurality of flow rates.

17. The device of claim 11, further comprising: a display device disposed in or attached to the housing, the display device configured to display a visual representation based on the indication.

18. The device of claim 11, further comprising: a communications device disposed in or attached to the housing, the communications device configured to communicate the indication to the remote system or device.

19. The device of claim 11, wherein the remote system or device comprises a processor executing the software application configured to plan or predict supply chain events, capital expenses, and/or delivery routes to customers.

20. The device of claim 11, wherein the remote system or device comprises the automated valve.

21. A non-transitory computer-readable medium for monitoring the mass of a fluid remaining in a tank as the fluid periodically or continuously leaves the tank through an automated valve, comprising program instructions that, when executed by at least one processor, cause the at least one processor to:
measure, with a flow meter in communication with the at least one processor, a plurality of flow rate measurements of the fluid as it leaves the tank during at least one measurement period, wherein each flow rate measurement of the plurality of flow rate measurements is determined at a time interval;

determine a mass of the fluid that has left the tank during the at least one measurement period based at least partially on: an averaged value of the plurality of flow rate measurements taken during the at least one measurement period, a density of the fluid at a pressure and/or temperature of the fluid as it passes through the flow meter, and the time interval between the plurality of flow rate measurements;

determine a mass of the fluid remaining in the tank based at least partially on a known, measured, or determined initial mass of the fluid in the tank and the determined mass of the fluid that has left the tank during the at least one measurement period;

generate, based at least partially on the mass of the fluid remaining in the tank, an indication of at least one of the following: a volume of the fluid remaining in the tank, a volume of the tank, a consumption rate, a consumption rate history, the determined mass of the fluid remaining in the tank, an estimated time remaining before the tank will be empty, or any combination thereof; and control the automated valve of the tank based at least partially on at least one of the mass of the fluid remaining in the tank and the indication.

* * * * *

UNITED STATES PATENT AND TRADEMARK OFFICE
CERTIFICATE OF CORRECTION

| | | |
|---|---|---|
| PATENT NO. | : 9,435,675 B2 | Page 1 of 1 |
| APPLICATION NO. | : 14/870828 | |
| DATED | : September 6, 2016 | |
| INVENTOR(S) | : Eric Christopher Wise | |

It is certified that error appears in the above-identified patent and that said Letters Patent is hereby corrected as shown below:

Title Page, Item (54) and in the Specification, Column 1, Line 3, Title, after "OF" insert -- A --

Signed and Sealed this
Sixth Day of December, 2016

Michelle K. Lee
*Director of the United States Patent and Trademark Office*